United States Patent
Steck et al.

(10) Patent No.: US 7,805,385 B2
(45) Date of Patent: Sep. 28, 2010

(54) PROGNOSIS MODELING FROM LITERATURE AND OTHER SOURCES

(75) Inventors: Harald Steck, Phoenixville, PA (US); Sriram Krishnan, Exton, PA (US); R. Bharat Rao, Berwyn, PA (US); Philippe Lambin, Genappe Bousvalle (BE); Cary Dehing-Oberije, Brunssum (NL)

(73) Assignee: Siemens Medical Solutions USA, Inc., Malvern, PA (US)

( * ) Notice: Subject to any disclaimer, the term of this patent is extended or adjusted under 35 U.S.C. 154(b) by 642 days.

(21) Appl. No.: 11/735,736

(22) Filed: Apr. 16, 2007

(65) Prior Publication Data
US 2008/0033894 A1    Feb. 7, 2008

Related U.S. Application Data

(60) Provisional application No. 60/792,544, filed on Apr. 17, 2006.

(51) Int. Cl.
G06E 1/00 (2006.01)
G06F 15/00 (2006.01)
G06G 7/00 (2006.01)
G06N 99/00 (2010.01)

(52) U.S. Cl. ...................................................... 706/10
(58) Field of Classification Search ...................... 706/10
See application file for complete search history.

(56) References Cited

U.S. PATENT DOCUMENTS

| | | |
|---|---|---|
| 2003/0120458 A1 | 6/2003 | Rao et al. |
| 2003/0125984 A1 | 7/2003 | Rao et al. |
| 2003/0125985 A1 | 7/2003 | Rao et al. |
| 2003/0126101 A1 | 7/2003 | Rao et al. |
| 2003/0130871 A1 | 7/2003 | Rao et al. |
| 2004/0172297 A1 | 9/2004 | Rao et al. |
| 2006/0265253 A1 | 11/2006 | Rao et al. |
| 2007/0118399 A1* | 5/2007 | Avinash et al. ............... 705/2 |

FOREIGN PATENT DOCUMENTS

| WO | WO 98/02837 A | 1/1998 |
|---|---|---|
| WO | WO 02/33654 A | 4/2002 |
| WO | WO 2005/091203 A | 9/2005 |

OTHER PUBLICATIONS

Selvin, "Lecture 5", www.biostat.jhsph.edu/~beglesto/, 2005.*
Futschik et al. "Prediction of clinical behaviour and treatment for cancers", OMJ Applied Bioinformatics, vol. 2(3), S53-58, 2003, pp. 1-15.*

(Continued)

*Primary Examiner*—Donald Sparks
*Assistant Examiner*—Li-Wu Chang
(74) *Attorney, Agent, or Firm*—Joshua B. Ryan

(57) ABSTRACT

A predictor of medical treatment outcome is developed and applied. A prognosis model is developed from literature. The model is determined by reverse engineering the literature reported quantities. A relationship of a given variable to a treatment outcome is derived from the literature. A processor may then use individual patient values for one or more variables to predict outcome. The accuracy may be increased by including a data driven model in combination with the literature driven model.

12 Claims, 6 Drawing Sheets

OTHER PUBLICATIONS

Nordsmark et al. "Prognostic value of tumor oxygenation in 397 head and neck tumors after primary radiation therapy. An international multi-center study", Radiotherapy and Oncology 77 (2005), pp. 18-24.*

Bellazzi et al. ("Integrating Rule-Based and Case-Based Decision Making in Diabetic Patient Management", ICCBR-99, LNAI 1650, pp. 386-400.*

* cited by examiner

Predictors included in the models

| | Model Knowledge | Logistic | RVM | Combined |
|---|---|---|---|---|
| Patient characteristics | | | | |
| Gender | x | x | x | x |
| Age | | | x | x |
| WHO-ps | x | | x | x |
| Nicotine use | | | x | x |
| FEV1 (liter) | | | x | x |
| FEV1 (%) | | x | | x |
| Tumor characteristics | | | | |
| Histology | x | | x | x |
| Overall stage | x | x | x | x |
| T-stage | | | x | x |
| Nodal stage | | x | | x |
| Treatment characteristics | | | | |
| Radiotherapy treatment dose | | x | | x |
| Overall treatment time (RT) | x | | | x |
| Chemotherapy | | | x | x |
| Imaging information | | | | |
| Gross tumor volume | | x | x | x |

PROGNOSIS MODELING FROM LITERATURE AND OTHER SOURCES

RELATED APPLICATIONS

The present patent document claims the benefit of the filing date under 35 U.S.C. §119(e) of Provisional U.S. Patent Application Ser. No. 60/792,544, filed Apr. 17, 2006, which is hereby incorporated by reference.

BACKGROUND

The present embodiments relate to prognosis modeling. Prognosis modeling attempts to predict the outcome, such as survivability, reoccurrence, effectiveness, and/or side effects, based on a proposed treatment or course of action. The prognosis modeling is performed for any desired disease, such as cancer.

There has been a steady increase of types of treatment for cancer, and thus treatment decision-making requires an assessment of risks and benefits associated with a specific combination of patient and treatment characteristics. Statistical models have proven useful for predicting prognosis and treatment outcome. These models are derived from the data collected at an institution. The data from other patients is used to create the model. The other patients are associated with different treatments and/or outcomes. The statistical model is formed by analyzing patient characteristics for these patients. However, data driven models typically require a large database of medical records representing previous treatment of many patients for statistical accuracy. Such databases may not be conveniently available or formatted for modeling. Using databases with records for a fewer number of medical records may provide less accuracy.

SUMMARY

In various embodiments, systems, methods, instructions, and computer readable media are provided for developing and/or applying a predictor of medical treatment outcome. A prognosis model is developed from literature. The model is determined by reverse engineering the literature reported quantities. A relationship of a given variable to a treatment outcome is derived from the literature. A processor may then use individual patient values for one or more variables to predict outcome. The accuracy may be increased by including models based on different sources, such as a data driven model in combination with the literature driven model.

In a first aspect, a system is provided for predicting medical treatment outcome. An input is operable to receive values for a plurality of patient specific characteristics of a patient. A processor is operable to apply the values to a first prognosis model. The first prognosis model relates a plurality of variables corresponding to the values to a treatment outcome, where the relating is a function of medical knowledge collected from literature and incorporated into the first prognosis model. A display is operable to output a patient specific prognosis for the patient as a function of the application of the values for the plurality of patient specific characteristics of the patient to the first prognosis model.

In a second aspect, a computer readable storage medium has stored therein data representing instructions executable by a programmed processor for predicting medical treatment outcome. The instructions include applying first and second prognosis models to individual patient information, the first and second prognosis models having different knowledge base sources; predicting a first treatment outcome with the first prognosis model from the individual patient information and as a function of quantities from clinical study publications as a first knowledge base source; and predicting a second treatment outcome with the second prognosis model from the individual patient information and as a function of model parameters from a database of past patient information for a plurality of patients as a second knowledge base source.

In a third aspect, a method is provided for developing a predictor of medical treatment outcome. Quantitative medical knowledge of predictors for a disease is collected from literature. A plurality of univariate relationships between a treatment and the predictors, respectively, are modeled from the quantitative medical knowledge. The models for the univariate relationships are combined into a multivariate model. A processor operates with the combined models as a prognosis model for an individual patient as a function of values for the predictors. The values are for the individual patient.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

FIG. 3 illustrates a table of one example of variables used in different prognosis models;

DESCRIPTION OF PREFERRED EMBODIMENTS

Treatment outcome is predicted using a model derived from published literature. Published literature is an available source of reliable information for modeling even where large databases are not available.

For increased accuracy, treatment outcome is predicted from statistical models that combine several sources of data, such as literature and data driven models. For example, 2-year survival of non-small-cell lung-cancer (NSCLC) patients is predicted based on individual or patient specific information. The prediction uses knowledge base gleaned from literature and a database. By incorporating both sources of information into a combined model, consistency and accuracy of the predictions may be improved.

The modeling may be associated with a healthcare workflow. For example, patient data mining or manual input provides values to one or more prognosis models. The values are for a particular patient. The model or models generate a prognosis regarding a possible treatment based on the values. The model or models may perform the prognosis iteratively to determine an optimal treatment, such as modeling different treatment possibilities. Alternatively, the suggested treatment is input manually and the prognosis associated with the treatment is output. Medical professionals may explore the treatment options best for a particular patient. The model or models provide a second source, based on a programmed medical knowledge base, for treatment recommendations or corresponding outcomes. The model or models indicate side effects, predicted survival rate, predicted reoccurrence rate, and/or other treatment based on the individual patient information. Any now known or later developed software or system providing a workflow engine may be configured to predict outcome based on data.

Figure 1:
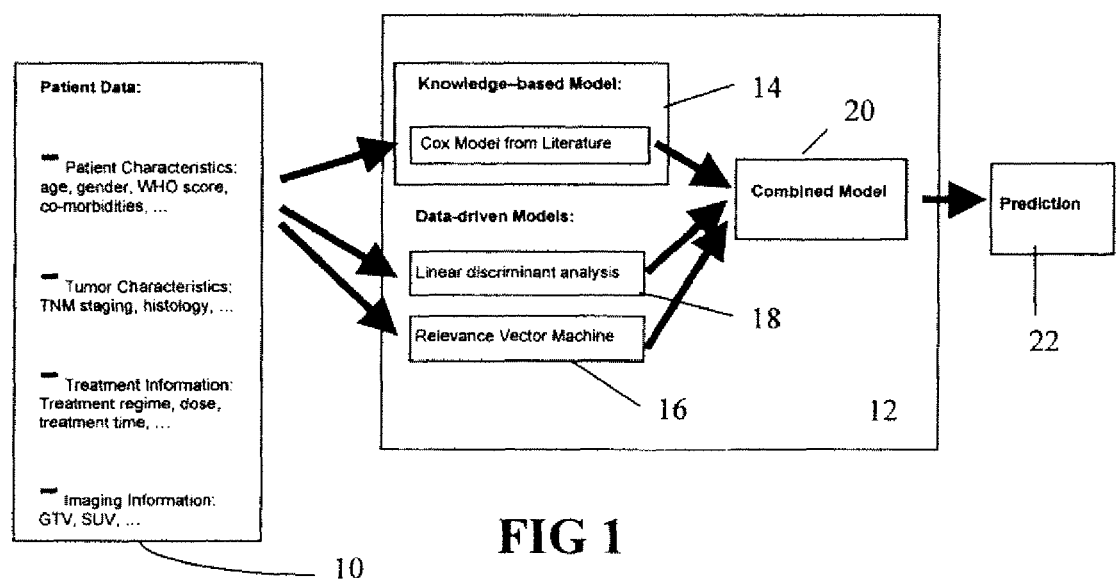
FIG. 1 is a block diagram of one embodiment of a method and/or system for applying prognosis models from different types of sources.

FIG. 1 shows a method for applying a predictor of medical treatment outcome. A prognosis model predicts one or more outcomes of treatment based on patient specific or an individual patient's characteristics. FIG. 1 also reflects one possible hardware embodiment. Patient data is provided at an input 10, such as from a medical database. Any patient information may be used, such as characteristics, treatment, imaging, tumor and/or other information. Patient characteristics may include age, gender, co-morbidities, performance score (WHO, Karnofsky) or others. Tumor characteristics may include Staging (e.g., tumor-node-metastasis (TNM) staging, according to the American Joint Committee on Cancer, AJCC), size, shape, number, location, histology, or others. Treatment information may include regime, dose, time, type, medicine, or others. Imaging information may include gross tumor volume (GTV), standard uptake value (SUV), or others.

The patient data is provided to a computer 12. The computer 12 applies one or more (three are shown) prognosis models 14, 16, 18 to all of or sub-sets of the input data. Example prognosis models include a literature based model and data driven models. The models may operate separately, and their outputs may be combined by the combing model 20. Alternatively, the models 14, 16, 18 are integrated into a unified single model. A predication is output to a display 22. Other embodiments may be provided as described below.

Figure 2:
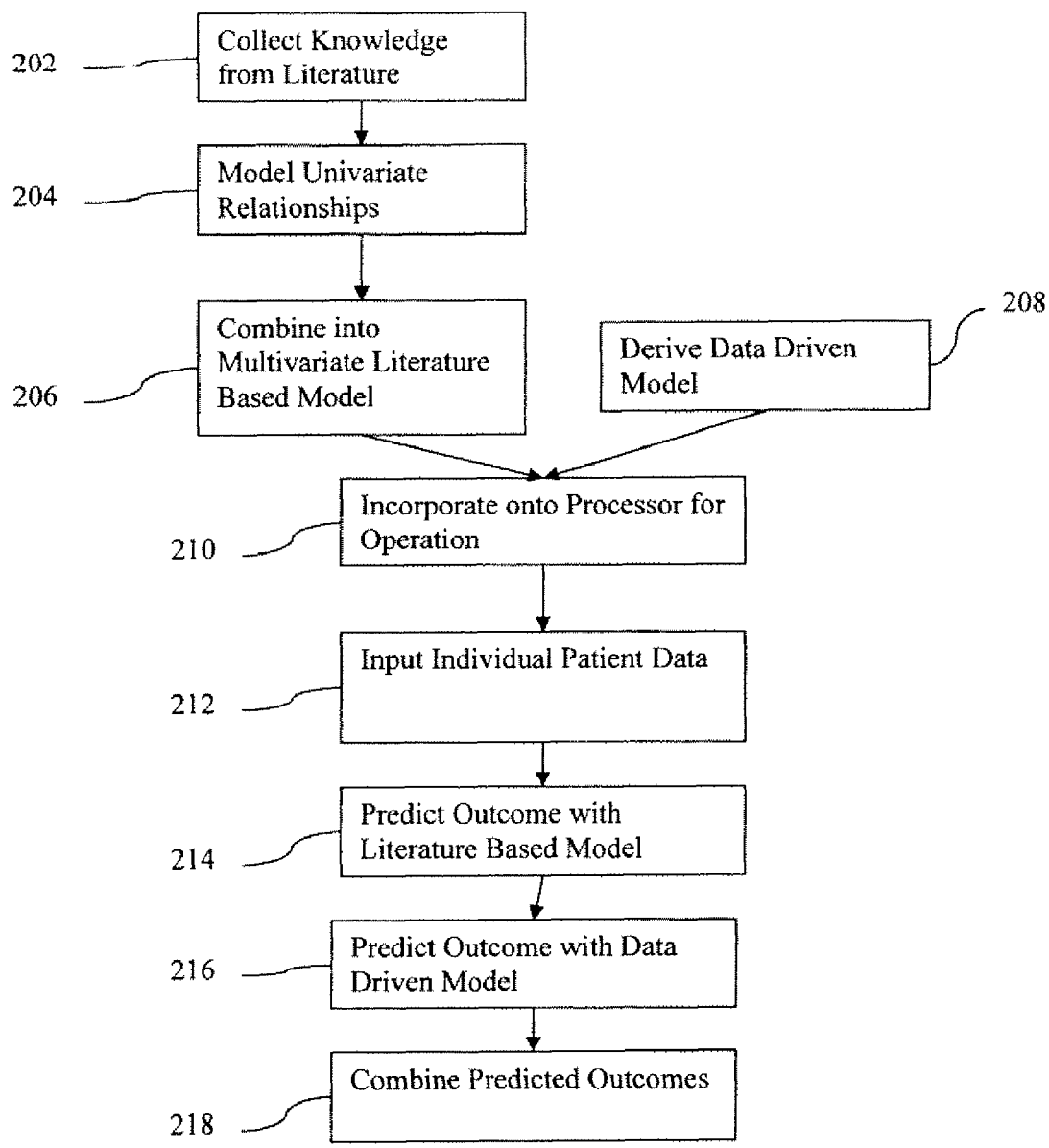
FIG. 2 shows one embodiment of a method for developing and applying a prognosis model.

FIG. 2 shows one embodiment of a method for developing one or more prognosis models and then applying the models as a predictor of medical treatment outcome. The method is implemented with the system of FIG. 1, the system of FIG. 4, or a different system. The same or different systems may perform the developing and applying stages. For example, one computer is used for development, and a different computer is used for applying the developed models. The models may be developed, and then sold or otherwise distributed for applications by others. As another example, the use of the developed models is charged. Users request predictions from the developer, so the model is applied by the same computer used for development or by different computer controlled by the developer.

The acts are performed in the order shown or a different order. Additional, different, or fewer acts may be provided. For example, act 208 is not provided. As another example, development acts (202, 204, 206, and 208) are performed without the application acts (212, 214, 216, and 218) or vice versa.

In act 202, quantitative medical knowledge of predictors for a disease is collected from literature. The literature is any published information, preferably credible. The literature sources may be books, medical journals, theses, reports, or other publication. One or more literature sources are used. For example, the leading or many publications associated with a particular disease are used.

The knowledge is collected for a specific disease or a group of related diseases. The knowledge reflects survivability, side effects, reoccurrence, and/or other outcome associated with one or more treatments. In one embodiment, the reported outcomes and corresponding treatments associated with a same disease are collected.

Any indication of a variable's correlation with outcome may be collected. The quantitative medical knowledge may be provided as a table, a graph, text, or combinations thereof. For example, the characteristics of the patient population targeted, the overall survival rates of the patient population, the survival rates of certain sub-populations exhibiting certain characteristics, the hazard ratio, fraction of patients in a study receiving treatment, grouping information, treatment, outcome, or other quantities are collected. Typically, the literature reports a study with two groups of patients, one group receiving a treatment and another group not receiving the treatment. The fraction of the patients between the two groups at the start of the study, the overall survival rate after a period, and the hazard ratio are given. In other publications, different, additional, or fewer information is provided. Values not reported directly may be inferred from the information provided in the literature, possibly requiring additional assumptions to make up for missing pieces of information.

The collection is performed manually. For example, one or more people review the literature and enter the information into a database or spread sheet. The collecting, review of the collection, or selection of sources to be used for collecting may be performed or reviewed by a doctor or other knowledgeable source. In an alternative embodiment, the information is collected automatically or semi-automatically. For example, the data mining discussed below is used to mine free text, other unstructured, or structured literature sources to collect the desired information. Combinations of manual and automatic may be performed.

In act 204, the relationship between the patient information and outcomes for each possible treatment is determined. In one embodiment, a multivariate model is created from the collected information without determining individual relationships. In another embodiment, univariate relationships between a treatment and different predictors (i.e., different patient information variables correlated with an outcome) are separately modeled from the quantitative medical knowledge. The statistical model and parameters underlying the reported results of the literature are reverse engineered from the collected data.

In one example embodiment, the literature includes a graph showing the outcome as a function of a variable. For example, the chance of surviving two years as a function of amount of smoking may be provided for a given treatment. By fitting a curve to the graph, a mathematical representation of the graph is provided for computer use. Linear, quadratic, or other fitting may be used. Alternatively, logic corresponding to the graph (e.g., if-then statements) models the graph.

In another example embodiment, the literature includes a table showing outcome as a function of the variable. The table is converted into logic statements for use by a computer. Alternatively, the table is used as data points for curve fitting. The fit curve models the table.

In yet another example embodiment, a binary classification is determined with a logistic or Cox regression. The classification is determined from a table, graph, text, or combinations thereof. Other modeling or classifications may be used. In other embodiments, a combination of models is determined for a univariate relationship, such as using both classification and curve fitting. Two different models represent the same relationship.

As an example of classification, an overall survival rate ($S_{av}$), a hazard ratio (h), and a fraction of study patients associated with different binary values (P=0 and P=1) of a variable being studied for correlation with outcome are collected and used for modeling one univariate relationship. The survival rate of each separate group of the patients may not be provided separately, so is modeled. For example, an overall survival rate is provided, but the separate survival rates for each of the two groups of patients are not provided. The separate survival rates are modeled.

Using a Cox regression model example for the binary predictor P, the collected data is classified. The value of the hazard ratio may be given as: $h=H_{P=0}/H_{P=1}$. The fraction of patients with P=0 and P=1 may be denoted by $w_{P=0}$ and $w_{P=1}$. The probability of 2-year survival for the sub-populations, denoted by $S_{P=0}$ and $S_{P=1}$, with P=0 and P=1 is inferred. The fraction is known at time zero (the beginning of the study), but not at the end of the study. An exponential, Weibull, or other distribution of the survival times is assumed or known. For an exponential decline, the equation: $w_{P=0}S_{P=1}{}^h+w_{P=1}S_{P=1}=S_{av}$ results. This equation includes the hazard ratio as an exponential term, the relative fractions as weights, the overall survival rate, and the desired two-year survival of one group of patients. The equation is solved (numerically) for $S_{P=1}$. The relationship of the two-year survival of the other group of patients is represented as: $S_{P=0}=(S_{av}-w_{P=1}S_{P=1})/w_{P=0}$. The results are probabilities of survival after two years for the binary predictor (variable).

In the example above, a specific regression model was used. Other models may be used, such as logistic regression. The outcome modeled in the example is survivability, but other outcomes may be modeled. The two-year survival was modeled, but other terms may be used. A range of times may be interpolated or extrapolated for a given predictor. Other equations may be used. Other quantities may be used. Non-binary modeling may be used. Other literature sources may give different types of information, so the modeling may be different based on context.

Different variable's relationship with outcome for a given treatment may be modeled. Different or the same modeling may be used. Any variable may be used, but statistically significant variables are preferred. Where available or desired, additional univariate relationships are modeled for a given treatment.

In act 206, the models for the univariate relationships are combined into a multivariate model. Any combination may be used. Since the relationships reflect probabilities, the combination may be probabilistic. For example, suppose a lung cancer patient has a 30% probability of two-year survival on average; and a smoker with lung cancer has a 27% probability of two-year survival, while a non-smoker with lung cancer has a 40% probability; moreover, suppose men with lung cancer have a 25% probability of two-year survival, while women have a 35% chance. Assuming that the gender of the patients and their smoking habits are independent of each other (which may not be true in practice), one can combine these two predictors, and obtain, for instance, that a non-smoking woman has a 45.6% chance of two-year survival, while a smoking man has a 22.3% probability of two-year survival.

As another possible combination, a Bayesian network is formed as the multivariate model from the univariate relationships. Bayesian networks serve as multivariate quantitative models that capture medical knowledge in the form of (probabilistic) causal effects. Other networks or combined models may be used.

The combination assumes the various univariate prediction models are independent of each other. Alternatively, the relationship between univariate prediction models is known or determined and included as part of the combination.

Apart from the literature, information obtained from physicians may be included in the literature model. The physician's knowledge may provide reasonable assumptions for filling in information missing in the literature or relationship between variables for forming the multivariate model. Other sources of information, such as derived from a database of patient records, may also be included, or maintained separately as a different prognosis model.

The modeling and combination of acts 204 and 206 are performed by a computer or manually. The models may be developed with the aid of a computer. The modeling and combination are programmed so that a computer may apply the resulting model to data for individual patients.

In act 208, a data driven model is derived. Any now known or later developed data driven model may be created, such as a linear discriminant analysis or relevance vector machine. Medical records for a plurality of patients are processed to model variables to outcome for one or more treatments. By mining or processing a database of patient information from previously treated patients, a model of values relationship to outcome is developed by a computer.

No, one, two or more data driven models may be derived. In one example for NSCLC patients shown in FIG. 1, two models are derived. One model is derived with a linear discriminant analysis (LDA). The predictors in this LDA model are chosen based on the literature, but may be selected from data analysis or by a physician. The model parameters are derived from the data available from an institution database of a plurality of previous patients. The other model is derived in a data-driven way using a relevance vector machine. The relevant predictors and the model parameters are both determined by the model or data processing.

The knowledge base used for each model is different or the same. For example, the multivariate model of act 206 is based on literature with or without physician provided information. The models in the example for act 208 above are based on a database. The literature driven model may be used as prior medical knowledge when learning the data driven model from the patient data. The prior medical knowledge is incorporated into machine learning from the database. The medical knowledge may be weighed against the information from the patient data for validation.

The model creation acts may be repeated for different treatments and/or outcomes. An array of models may be provided in order to explore the possible outcomes associated with different options for a same patient.

In act 210, the models are incorporated onto a computer, such as into hardware, software, or both. The incorporation allows operating, with a processor, combined models or a single model as a prognosis model for an individual patient. Values for the predictors of the models are obtained. The medical record or other source provides values for a specific or individual patient. The model is applied to the individual patient information. In the example of FIG. 1, both the data driven model and the literature driven model from acts 206 and 208 are applied.

Separate outputs from the different models may be provided. Alternatively, the models are incorporated to provide a single output or related outputs. The combined model may be an improved prediction-model based on multiple sources of information.

Any combination may be used. In one embodiment, the predictions are combined as an ensemble. The prediction of the different models is combined, such as a weighted average or majority vote. Different models may use different predictors or variables for input. FIG. 3 shows one example. If the models to be combined have the same input variables or predictors, then the models may be fused. The models are combined to form a single model, such as a Bayesian network.

In act 212, individual patient data is input for application of the prognosis model. The data input corresponds to the predictors or variables used by the models. Where a value for an individual patient is not available, a value may be assumed, such as using an average.

The data is input manually. Alternatively, the data is mined from a structured database. If values are available from unstructured data, the values may be mined by searching or probabilistic inference. A processor mines the values from a medical record of the individual patient. For example, the mining discussed below is performed. The mined and/or manually input values are applied to the combined models to obtain an outcome prediction, such as a survival rate for a treatment of the individual patient.

In act 214, a treatment outcome is predicted with the literature-based model. The treatment may be a lack of further action, chemotherapy, type of drug, amount of drug, radiation, type of radiation, radiation timing, or other treatment, or treatment combination. The literature-based model is derived from quantities in clinical study publications as a knowledge base source. The patient specific information is input to the model as values for variables identified from the literature. The application results in one or more predicted treatment outcomes.

In one embodiment, the literature-based model of FIG. 1 was applied. The model used relevant predictors for which consistent results and hazard ratios were reported in the literature for NSCLC. NSCLC after chemo or radiotherapy was evaluated for patients at stage I to IIIB. There has been a steady increase of different types of treatment for lung cancer and thus treatment decision making requires an assessment of risks and benefits associated with a specific combination of patient and treatment characteristics. To evaluate NSCLC models, a knowledge-based model was derived from the literature, combining the information from several individual studies, each of which was based on a limited patient population. The knowledge-based model was for 2-year survival. The variables identified in the literature were overall stage, gender, WHO-ps, histology, and overall treatment time.

A five-fold cross validation on patient-data from the MAASTRO clinic in the Netherlands was performed. Performance of a model may be expressed as the area under the curve (AUC) of the receiver operator curve (ROC). The maximum value of the AUG is 1.0, indicating a perfect prediction model. A value of 0.5 indicates that patients are correctly classified in 50% of the cases. For the literature-based model, the AUG was 0.73 on data for 124 NSCLC patients. Using the same database updated to include 246 patients, the AUG was 0.67.

In act 216, another or the same treatment outcome is predicted with another prognosis model. The same or different data for the individual patient is input. The other prognosis model is based on a different source of information, such as a data driven model. The model operates as a function of model parameters with a database of past patient information for a plurality of patients as a knowledge base source.

In the example of FIG. 1, two different data driven models were applied. In one model, a multivariate logistic regression model used an initial set of predictors chosen based on literature. The variables selected were overall stage, nodal stage, gender, gross tumor volume (GTV), radiotherapy treatment dose, and forced expiratory volume in 1 sec in % (FEV1). A stepwise backward method was used to remove non-significant factors from the model and to obtain the model parameters. The resulting cross-validated AUCs were 0.71 (database of 124 patients) and 0.70 (database of 246 patients).

In the other model, a relevance vector machine (RVM) model used the database data to select relevant predictors and learn the model parameters. The resulting variables were gender, overall stage, gross tumor volume (GTV), performance scale (WHO-ps), histology, age, nicotine use, chemotherapy, forced expiratory volume in 1 sec (in liter) and T-stage. This model yielded cross-validated AUCs of 0.76 (n=124) and 0.71 (n=246).

FIG. 3 shows one embodiment of the variables included in the models of FIG. 1. The variables are broken down by the type of information represented. The knowledge model is the literature-based model.

In act 218, the predicted outcomes are combined, if more than one predicted outcome is used. For a single or combined prognosis model, a single outcome for a same consideration (e.g., two-year survival) may be provided. In other embodiments, separate models predict the outcome for a same consideration. Any combination may be used.

In the example of FIG. 1, the outputs from the three models were combined using an ensemble method (weighted average). For the initial cross-validation database (124 patients), the output of the knowledge-based literature model was weighted by 0.7, the output of the linear discriminant analysis was weighted by 0.2, and the output of the relevance vector machine was weighted with 0.1. The resulting AUG was 0.82 for the small dataset. Regarding the final data set of 246 patients for cross validation, the weight of the knowledge-based literature model decreased to 0.4, and the weights of the other two models increased to 0.3 each. The resulting AUG was 0.72, remaining almost constant for the large data set. The standard deviation of the AUCs was 0.1 for the small data set, and 0.08 for the large one. Additional refinements of the prediction model may be achieved by integrating even more sources of information, like ones concerning molecular markers. By providing models corresponding to different treatments, a model may optimize treatment plans based on individual patient characteristics. These results suggest that combining clinical data (data-driven) with literature-based medical knowledge may result in models that are more accurate from small patient populations, allowing further individualization of treatment in the future.

Figure 4:
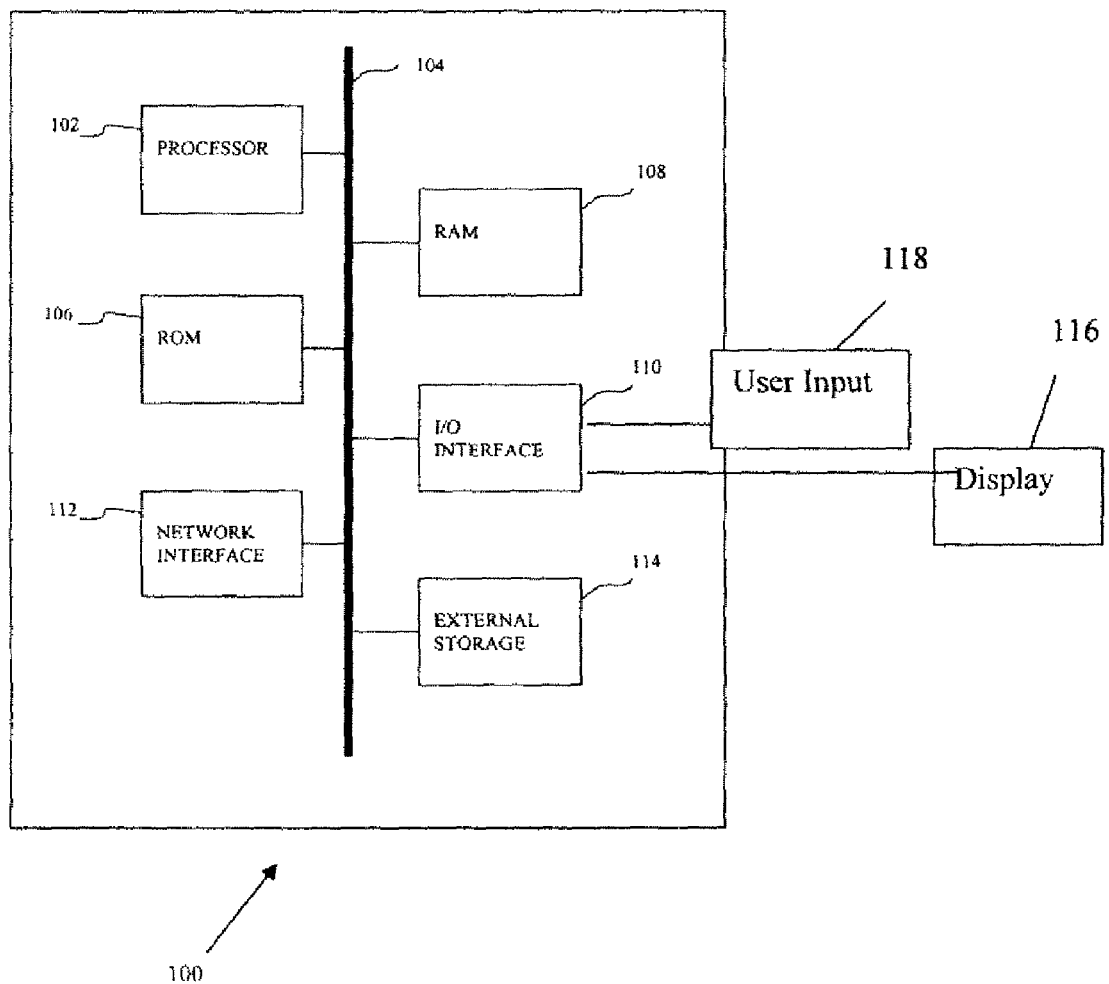
FIG. 4 is a block diagram of one embodiment of a system for applying a prognosis model.

FIG. 4 shows is a block diagram of an example system 100 for predicting medical treatment outcome. The system 100 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated workflows are provided to assist a user in generating a predication of treatment outcome.

The system 100 is a computer, personal computer, server, PACs workstation, imaging system, medical system, network processor, network, or other now know or later developed processing system. The system 100 includes at least one processor (hereinafter processor) 102 operatively coupled to other components via a system bus 104. The processor 102 is implemented on a computer platform having hardware components. The other components include memories (ROM 106 and/or RAM 108), a network interface 112, an external storage 114, an input/output interface 110, a display 116, and the user input 118. Additional, different, or fewer components may be provided.

The computer platform also includes an operating system and microinstruction code. The various processes, methods, acts, and functions described herein may be either part of the microinstruction code or part of a program (or combination thereof) which is executed via the operating system.

The user input 118, network interface 112, or external storage 114 may operate as an input operable to receive values for a plurality of patient specific characteristics of a patient. The values are for variables to be used by one or more models. The values may be manually input or input by a processor, such as inputting as part of mining from a database in the external storage 114 or elsewhere.

The user input 118 is a mouse, keyboard, track ball, touch screen, joystick, touch pad, buttons, knobs, sliders, combinations thereof, or other now known or later developed input device. The user input 118 operates as part of a user interface. For example, one or more buttons are displayed on the display 116. The user input 118 is used to control a pointer for selection and activation of the functions associated with the buttons. Alternatively, hard coded or fixed buttons may be used.

Referring to FIG. 1, the network interface 112 may be a hard-wired interface. However, in various exemplary embodiments, the network interface 112 may include any device suitable to transmit information to and from another device, such as a universal asynchronous receiver/transmitter (UART), a parallel digital interface, a software interface or any combination of known or later developed software and hardware. The network interface 112 may be linked to various types of networks, including a local area network (LAN), a wide area network (WAN), an intranet, a virtual private network (VPN), and the Internet.

The processor 102 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 102. The processor 102 implements the program alone or includes multiple processors in a network or system for parallel or sequential processing.

The processor 102 performs the workflows, data mining, model development, model application, and/or other processes described herein. For example, the processor 102 or a different processor is operable to extract values for the desired variables. The processor 102 applies the values to a prognosis model relating a plurality of variables corresponding to the values to a treatment outcome. In one embodiment, each variable relates to a probability for outcome. The probabilities for the values for the various variables are combined by the processor 102 for applying the model. The relationships may have been elicited from medical doctors.

The processor 102 applies the same values and/or additional values for the patient to another prognosis model in one embodiment. The other prognosis model is derived from a different knowledge base, such as being a statistical model derived from a database of patient data for a plurality of patients. The processor 102 may apply values to other prognosis models, such as another statistical prognosis model device from a database. The variables used for the different models are the same or different, with or without overlap.

The processor 102 outputs the predicted outcome on the display 116, into a memory, over a network, to a printer, or in another media. The display 116 is a CRT, LCD, plasma, projector, monitor, printer, or other output device for showing data. The display 116 is operable to display the predicted outcome or a plurality of outcomes. The display is text, graphical, or other display. A patient specific prognosis for the patient as a function of the application of the values for the plurality of patient specific characteristics of the patient to the one or more prognosis models is output. The patient specific prognosis is a function of outputs from the one or more prognosis models. Supporting information, such as values, different model outputs, options, or other supporting information, may be displayed with the outcome.

The processor 102 operates pursuant to instructions. The instructions and/or patient record for predicting medical treatment outcome are stored in a computer readable memory, such as the external storage 114, ROM 106, and/or RAM 108. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

Figure 5:
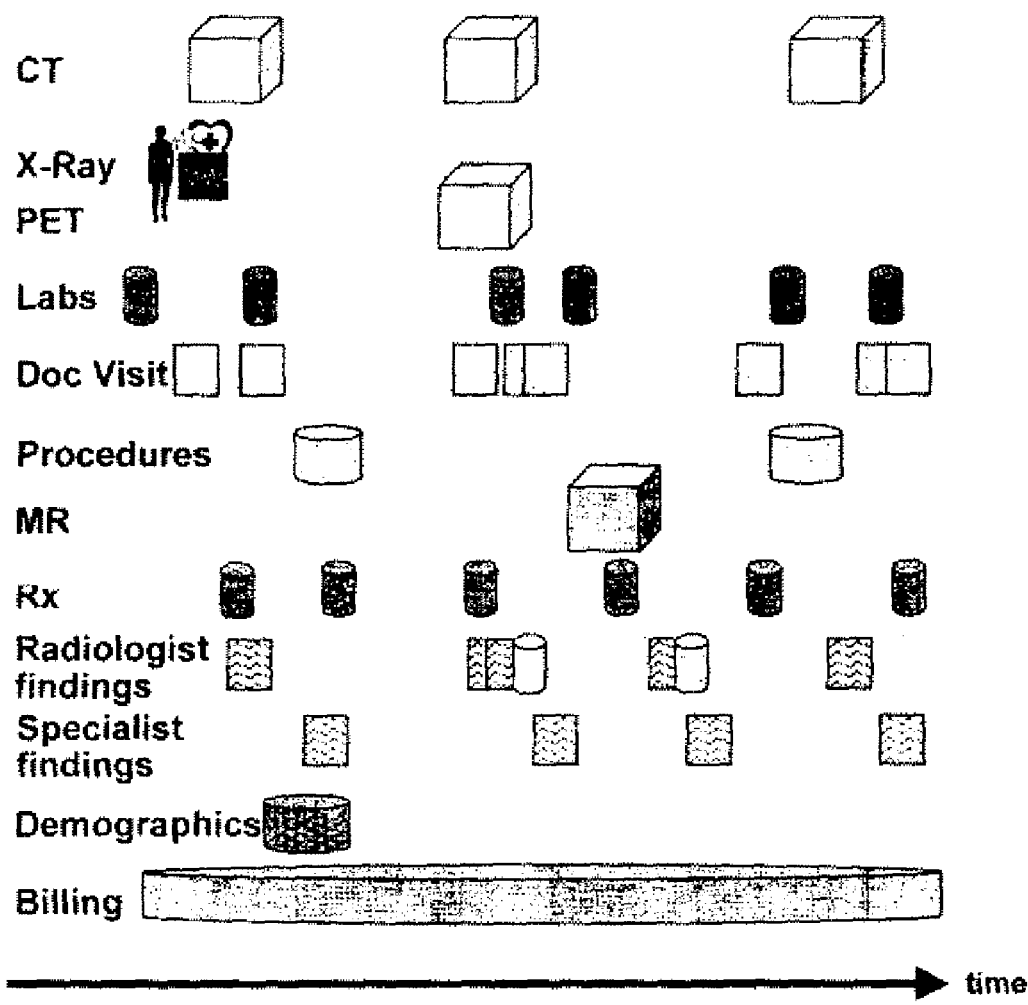
FIG. 5 is a graphical representation of a patient medical record in one example.

The same or different computer readable media may be used for the instructions, the individual patient record data, and the database of previously treated patients. The patient records are stored in the external storage 114, but may be in other memories. The external storage 114 may be implemented using a database management system (DBMS) managed by the processor 102 and residing on a memory, such as a hard disk, RAM, or removable media. Alternatively, the storage 114 is internal to the processor 102 (e.g. cache). The external storage 114 may be implemented on one or more additional computer systems. For example, the external storage 114 may include a data warehouse system residing on a separate computer system, a PACS system, or any other now known or later developed hospital, medical institution, medical office, testing facility, pharmacy or other medical patient record storage system. The external storage 114, an internal storage, other computer readable media, or combinations thereof store data for at least one patient record for a patient. The patient record data may be distributed among multiple storage devices as represented in FIG. 5 or in one location.

Increasingly, health care providers are employing automated techniques for information storage and retrieval. The use of a computerized patient record (CPR) to maintain patient information is one such example. As shown in FIG. 5, an exemplary CPR 200 includes information collected over the course of a patient's treatment or use of an institution. This information may include, for example, computed tomography (CT) images, X-ray images, laboratory test results, doctor progress notes, details about medical procedures, prescription drug information, radiological reports, other specialist reports, demographic information, family history, patient information, and billing (financial) information.

A CPR may include a plurality of data sources, each of which typically reflects a different aspect of a patient's care. Alternatively, the CPR is integrated into one data source. Structured data sources, such as financial, laboratory, and pharmacy databases, generally maintain patient information in database tables. Information may also be stored in unstructured data sources, such as, for example, free text, images, and waveforms. Often, key clinical findings are only stored within unstructured physician reports, annotations on images or other unstructured data source.

The database for deriving data driven models may be in the form of a CPR 200. Data for a plurality of patients having been previously treated are stored. Alternatively or additionally, the medical records for the individual to be treated are stored in the CPR 200.

In one embodiment, the patient values for application by the models and/or the data for a data-driven model development are mined from patient medical records. Any now known or later developed data mining may be used. For structured medical records, different search routines may be used based on the structure. For unstructured or structured and unstructured medical records, probabilistic inference is used for mining in one embodiment. The mining is performed by a processor. For mining, facts are extracted from a patient record. The facts may be data points indicating a conclusion. The facts may or may not be accurate.

Patient records are mined for information related to a plurality of values corresponding to variables or possible variables used in modeling. In some situations, the patient record may be distributed or stored at different institutions. Different institutions include doctor's offices, hospitals, health care networks, clinics, imaging facility or other medical group. The different institutions have separate patient records, but may or may not be affiliated with each other or co-owned. In order to mine the patient records, the patient records from the different institutions are linked. As an example, consider a guideline from *The Specifications Manual for National Hospital Quality Measures*. If a patient is admitted to the hospital with a primary diagnosis of heart failure, then there should be documentation of left ventricular systolic function (LVSF) assessment at any time prior to arrival or during the hospitalization. First, the hospital records are searched to find patients who were admitted with a primary diagnosis of heart failure. This can be done by searching the records (e.g., billing records and/or other data sources) of a hospital. To assess the second part, however, is a little more complicated. If a mention of LVSF assessment exists in the hospital records, as part of the history, discharge summary, or somewhere else, then the data can be assessed from the hospital data alone. Often, however, the data is not available there, but elsewhere. For example, if the patient was referred to the hospital by his cardiologist, who performed the LVSF assessment in his office the previous day, then the record of LVSF assessment is with the physician in his practice notes. If the LVSF assessment was done at one hospital, and then the patient was transferred to the current hospital, then the record of the LVSF assessment is with the previous hospital.

The values for modeling or to be applied to a model are derived from the extracted information. The values are determined from one or more data points. The values may be derived as part of the extraction. For example, the values are derived probabilistically by combining factoids. The values may be derived from already extracted information. Non-probabilistic derivation may be used.

Example embodiments for data mining include mining from unstructured patient records using probabilities. U.S. Published Application No. 2003/0120458 discloses mining unstructured and structured information to extract structured clinical data. Missing, inconsistent or possibly incorrect information is dealt with through assignment of probability or inference. These mining techniques are used for quality adherence (U.S. Published Application No. 2003/0125985), compliance (U.S. Published Application No. 2003/0125984), clinical trial qualification (U.S. Published Application No. 2003/0130871), billing (U.S. Published Application No. 2004/0172297), and improvements (U.S. Published Application No. 2006/0265253). The disclosures of these published applications referenced above are incorporated herein by reference. Other patient data mining or mining approaches may be used, such as mining from only structured information, mining without assignment of probability, or mining without inferring for inconsistent, missing or incorrect information.

Figure 6:
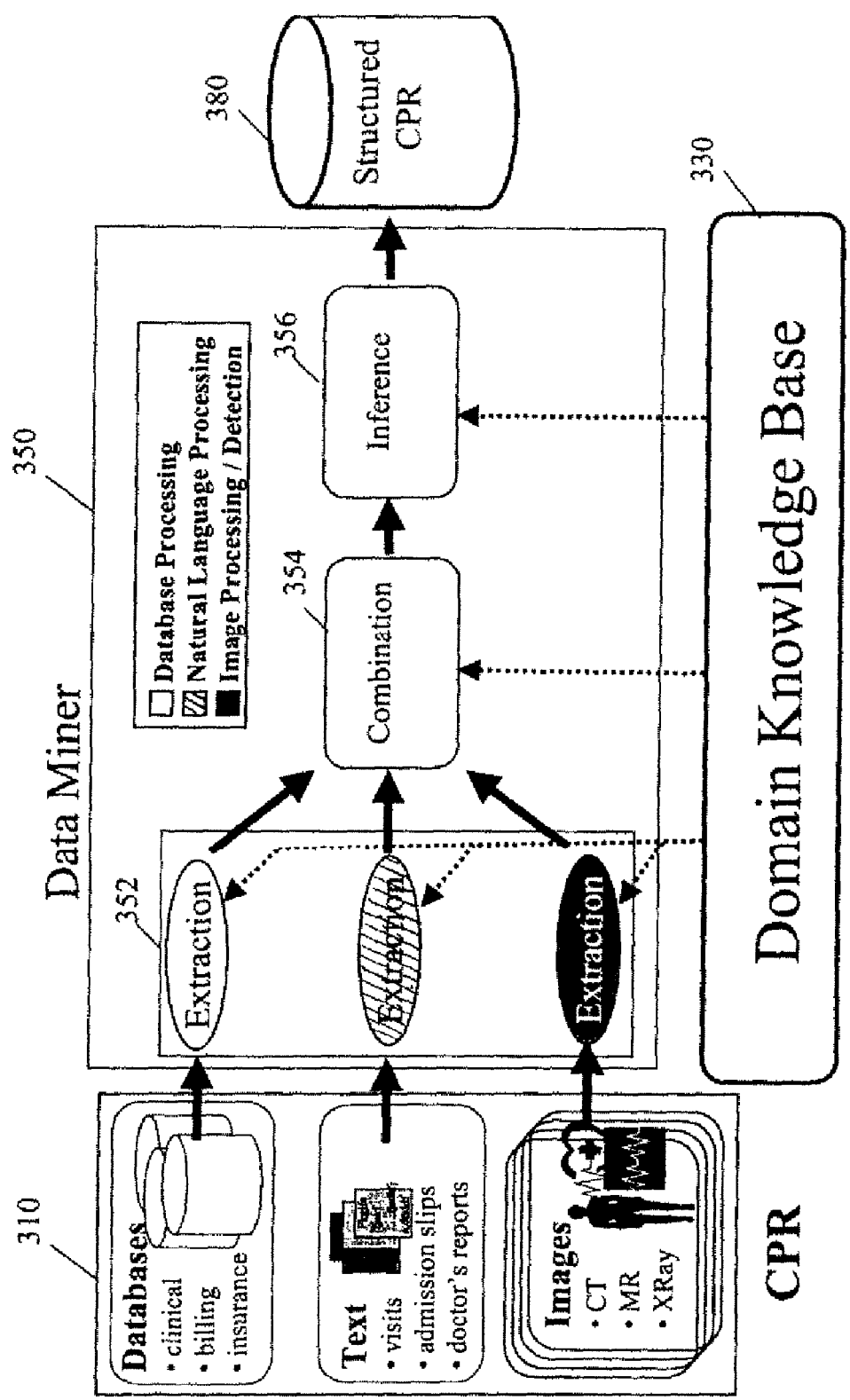
FIG. 6 is a graphical representation of one embodiment of a data miner for deriving individual patient input for a prognosis model.

The processor 102 or a different processor mines the patient records and automatically extracts values. FIG. 6 illustrates an exemplary data mining system implemented by the processor 102 for mining a patient record to create high-quality structured clinical information. The processing components of the data mining system are software, firmware, microcode, hardware, combinations thereof, or other processor based objects. The data mining system includes a data miner 350 that mines information from a computerized patient record (CPR) 310 using domain-specific knowledge contained in a knowledge base 330. The data miner 350 includes components for extracting information from the CPR 352, combining all available evidence in a principled fashion over time 354, and drawing inferences from this combination process 356. The mined information may be stored in a structured CPR 380. The architecture depicted in FIG. 3 supports plug-in modules wherein the system can be easily expanded for new data sources, diseases, and hospitals. New element extraction algorithms, element combining algorithms, and inference algorithms can be used to augment or replace existing algorithms.

The mining is performed as a function of domain knowledge. Detailed knowledge regarding the domain of interest, such as, for example, a disease of interest, guides the process to identify relevant information. This domain knowledge base 330 can come in two forms. It can be encoded as an input to the system, or as programs that produce information that can be understood by the system. For example, a clinical guideline to diagnosing a particular disease or diseases provides information relevant to the prognosis. The clinical guideline is used as domain knowledge for the mining. The domain knowledge may be provided from literature sources associated with prognosis. Additionally or alternatively, the domain knowledge base 330 may be learned from test data as a function or not as a function of an otherwise developed clinical guideline. The learned relationships of information to a diagnosis or prognosis may be a clinical guideline.

The domain-specific knowledge may also include disease-specific domain knowledge. For example, the disease-specific domain knowledge may include various factors that influence risk of a disease, disease progression information, complications information, outcomes, and variables related to a disease, measurements related to a disease, and policies and guidelines established by medical bodies. The domain-specific knowledge base may include synonyms, terms, or other indicators determined to be relevant to a particular condition, guideline, or influencing factors.

The information identified as relevant by the clinical guideline provides an indication of probability that a factor or item of information indicates or does not indicate a particular diagnosis or prognosis. The relevance may be estimated in general, such as providing relevance for any item of information more likely to indicate a diagnosis or prognosis as 75% or other probability above 50%. The relevance may be more specific, such as assigning a probability of the item of information indicating a particular prognosis based on clinical experience, tests, studies or machine learning. The domain knowledge indicates elements with a probability greater than a threshold value of indicating the patient state, diagnosis, desired data point, value, prognosis, or measure. Other probabilities may be associated with combinations of information.

Domain-specific knowledge for mining the data sources may include institution-specific domain knowledge. For example, information about the data available at a particular hospital, document structures at a hospital, policies of a hospital, guidelines of a hospital, and any variations associated with a hospital. The domain knowledge guides the mining, but may guide without indicating a particular item of information from a patient record.

The extraction component 352 deals with gleaning small pieces of information from each data source regarding a patient or plurality of patients. The pieces of information or elements are represented as probabilistic assertions about the patient at a particular time. Alternatively, the elements are not associated with any probability. The extraction component 352 takes information from the CPR 310 to produce probabilistic assertions (elements) about the patient that are relevant to an instant in time or period. This process is carried out with the guidance of the domain knowledge that is contained in the domain knowledge base 330. The domain knowledge for extraction is generally specific to each source, but may be generalized.

The data sources include structured and/or unstructured information. Structured information may be converted into standardized units, where appropriate. Unstructured information may include ASCII text strings, image information in DICOM (Digital Imaging and Communication in Medicine) format, or text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge encodes what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images or waveforms may be carried out by image processing or feature extraction programs that are provided to the system. Extraction from a text source may be carried out by phrase spotting, which requires a list of rules that specify the phrases of interest and the inferences that can be drawn there from. For example, if there is a statement in a doctor's note with the words "there is evidence of metastatic cancer in the liver," then, in order to infer from this sentence that the patient has cancer, a rule directs the system to look for the phrase "metastatic cancer." If the phrase is found, an assertion that the patient has cancer with a high degree of confidence (which, in the present embodiment, translates to generate an element with name "Cancer", value "True" and confidence 0.9) is generated.

The combination component 354 combines all the elements that refer to the same variable at the same period to form one unified probabilistic assertion regarding that variable. Combination includes the process of producing a unified view of each variable at a given point in time from potentially conflicting assertions from the same/different sources. These unified probabilistic assertions are called factoids. The factoid is inferred from one or more elements. Where the different elements indicate different factoids or values for a factoid, the factoid with a sufficient (threshold) or highest probability from the probabilistic assertions is selected. The domain knowledge base may indicate the particular elements used. Alternatively, only elements with sufficient determinative probability are used. The elements with a probability greater than a threshold of indicating a patient state (e.g., directly or indirectly as a factoid), are selected. In various embodiments, the combination is performed using domain knowledge regarding the statistics of the variables represented by the elements ("prior probabilities").

The patient state is an individual model of the state of a patient. The patient state is a collection of variables that one may care about relating to the patient, such as established by the domain knowledgebase. The information of interest may include a state sequence, i.e., the value of the patient state at different points in time during the patient's treatment.

The inference component 356 deals with the combination of these factoids, at the same point in time and/or at different points in time, to produce a coherent and concise picture of the progression of the patient's state over time. This progression of the patient's state is called a state sequence. The patient state is inferred from the factoids or elements. The patient state or states with a sufficient (threshold), high probability or highest probability are selected as an inferred patient state or differential states.

Inference is the process of taking all the factoids and/or elements that are available about a patient and producing a composite view of the patient's progress through disease states, treatment protocols, laboratory tests, clinical action, or combinations thereof. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, or other information). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer <cancer=True (probability=0.35), cancer=False (probability=0.65)> (e.g., 35% of patients have cancer). Then, this assertion is combined with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer=True (probability=0.1), cancers=unknown (probability=0.9)> and
4. <cancer=False (probability=0.4), cancer=unknown (probability=0.6)>.

In this case, we might combine these elements with the base probability of cancer <cancer=True (probability=0.35), cancer=False (probability=0.65)> to conclude, for example, that <cancer=True (prob=0.67), cancer=False (prob=0.33)>.

In alternative embodiments, specific probabilistic conclusions are determined without mining for an overall or temporal patient state. For example, the values for prognosis prediction are extracted without determining a progression of conditions or other history associated with a patient.

Numerous data sources may be assessed to gather the elements, and deal with missing, incorrect, and/or inconsistent information. As an example, consider that, in determining whether a patient has diabetes, the following information might be extracted:
  (a) ICD-9 billing codes for secondary diagnoses associated with diabetes;
  (b) drugs administered to the patient that are associated with the treatment of diabetes (e.g., insulin);
  (c) patient's lab values that are diagnostic of diabetes (e.g., two successive blood sugar readings over 250 mg/d);
  (d) doctor mentions that the patient is a diabetic in the H&P (history & physical) or discharge note (free text); and
  (e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. These observations (e.g., about the billing codes, the drugs, the lab tests, etc.) may be probabilistically combined to come up with a final probability of diabetes. Note that there may be information in the patient record that contradicts diabetes. For instance, the patient has some stressful episode (e.g., an operation) and his blood sugar does not go up. In another example, observations of ST-elevations in an EKG can increase confidence that the patient had a heart attack, even though the ST-elevations alone are not conclusive evidence of a heart attack.

The above examples are presented for illustrative purposes only and are not meant to be limiting. The actual manner in which elements are combined depends on the particular domain under consideration as well as the needs of the users of the system. Further, while the above discussion refers to a patient-centered approach, multiple patients may be handled simultaneously. Additionally, a learning process may be incorporated into the domain knowledge base 330 for any or all of the stages (i.e., extraction, combination, inference).

In the case of missing information, no supporting evidence is found. The processor 102 may respond in one of two ways. The field may be left blank, or a prior probability is used to compute the most likely response. For example, one of the questions asked is whether the patient is a smoker or not. If there is no evidence provided in the patient record if the user is a smoker, then the system leaves this blank or records that the user is not a smoker, since the prior probability (based on the percentage of smokers) suggests that the patient is probably not a smoker.

The mining may be run using the Internet. The created structured clinical information may also be accessed using the Internet. Additionally, the data miner may be run as a service. For example, several hospitals may participate in the service to have their patient information mined for compliance, and this information may be stored in a data warehouse owned by the service provider. The service may be performed by a third party service provider (i.e., an entity not associated with the hospitals).

The domain knowledgebase, extractions, combinations and/or inference may be responsive or performed as a function of one or more parameter values. For example, the probabilistic assertions may ordinarily be associated with an average or mean value. However, some medical practitioners or institutions may desire that a particular element be more or less indicative of a patient state. A different probability may be associated with an element. As another example, the group of elements included in the domain knowledge base for a particular disease or clinical guideline may be different for different people or situations. The threshold for sufficiency of probability or other thresholds may be different for different people or situations.

The mining generates data points and/or values. Once the structured CPR 380 is populated with patient information, data points are provided in a form conducive for answering questions regarding prognosis, such as determining values for modeled predictors or variables. The structured information may include the values in addition to data points used to derive the values. For example, the factoids and the combined information are included as extracted or structured information.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for predicting medical treatment outcome, the system comprising:
  an input that receives values for a plurality of patient specific characteristics of a patient;
  a processor configured to apply the values to a first prognosis model, the first prognosis model comprising a multivariate regression, the first prognosis model relating a plurality of variables, corresponding to the values, to a treatment outcome, the relating being a function of medical knowledge of a result associated with treatment, the medical knowledge collected from literature pertaining to a disease or diseases and incorporated into the first prognosis model, the processor is configured to apply the values or additional values of the patient specific characteristics of the patient to a second prognosis model, the second prognosis model being a statistical data-driven model derived from a database of patient medical records for a plurality of patients, the first and second prognosis models being for the same treatment outcome, the processor configured to output a patient specific prognosis for the patient based on a combination of outputs from the first and second prognosis models; and a display that displays the patient specific prognosis for the patient as a function of the application of the values for the plurality of patient specific characteristics of the patient to the first and second prognosis models.

2. The system of claim 1 wherein the input comprises a data interface configured to receive the values mined from data by the processor or a different processor.

3. The system of claim 1 wherein the relating performed by the processor is a function of relationships elicited from medical doctors.

4. The system of claim 1 wherein the relating performed by the processor is a function of probabilities corresponding to individual predictors modeled for each variable.

5. The system of claim 1 wherein the first prognosis model is a function of medical knowledge collected from literature converted into a functional relationship for each variable independent of other variables.

6. The system of claim 1 wherein the relating is determined by modeling a continuous-time relationship from one or more discrete relationships from the literature.

7. The system of claim 1 wherein the processor is configured to apply the values or additional values of the patient to a third prognosis model, the third prognosis model being a statistical model derived from the database of patient medical records for the plurality of patients, different values or additional values applied to the second prognosis model than for the third prognosis model, the different values or additional values for the second prognosis model being based on the literature and for the third prognosis model being based on the database.

8. The system of claim 1 wherein the patient specific prognosis is a function of outputs from the first and second prognosis models, the outputs being for a same prediction.

9. The system of claim 1 wherein the relating performed by the processor for one variable is a function of probabilities derived from a hazard ratio, a survival rate, and a fraction receiving a treatment option, the hazard ratio, the survival rate and the fraction provided in the literature, the first prognosis model incorporating a survival rate for the treatment option derived from the hazard ratio, the survival rate, and the fraction.

10. In a computer readable, non-transitory storage medium having stored therein data representing instructions executable by a programmed processor for predicting medical treatment outcome, the instructions comprising:

applying first and second prognosis models to individual patient medical records, the first and second prognosis models having different knowledge base sources, the first prognosis model comprising a multivariate regression;

predicting a first treatment outcome for a first treatment with the first prognosis model from the individual patient medical records and as a function of quantities from clinical study publications as a first knowledge base source, the quantities determined from results associated with the first treatment, the results from the publications being used to derive the quantities;

predicting a second treatment outcome for the first treatment with the second prognosis model from the individual patient medical records and as a function of model parameters from a database of past patient medical records for a plurality of patients as a second knowledge base source; and combining the first and second treatment outcomes into a third treatment outcome.

11. The instructions of claim 10 wherein predicting with the first and second prognosis models comprises predicting with a combined prognosis model fusing the first and second prognosis models.

12. The instructions of claim 10 wherein predicting the first treatment outcome comprises:

inputting the individual patient medical records, the medical records comprising values for variables identified in the clinical study publications as correlated with the first treatment outcome;

applying each of the values to a corresponding survival rate as a function of time derived from a survival rate at a given time from the clinical study publication; and probabilistically combining outputs from each of the applications for corresponding values, the combination being the first treatment outcome.

* * * * *